(12) United States Patent
Mikami et al.

(10) Patent No.: US 11,168,043 B2
(45) Date of Patent: Nov. 9, 2021

(54) METHOD AND APPARATUS FOR PRODUCING 1,2,3,4-TETRACHLOROBUTANE

(71) Applicant: SHOWA DENKO K.K., Tokyo (JP)

(72) Inventors: Katsumi Mikami, Tokyo (JP); Yohsuke Fukuchi, Tokyo (JP); Shinya Oguro, Tokyo (JP); Hiroshi Kobayashi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/981,814

(22) PCT Filed: Mar. 1, 2019

(86) PCT No.: PCT/JP2019/008097
§ 371 (c)(1),
(2) Date: Sep. 17, 2020

(87) PCT Pub. No.: WO2019/181439
PCT Pub. Date: Sep. 26, 2019

(65) Prior Publication Data
US 2021/0017105 A1   Jan. 21, 2021

(30) Foreign Application Priority Data
Mar. 20, 2018 (JP) .............. JP2018-052451

(51) Int. Cl.
*C07C 17/013* (2006.01)
*C07C 17/04* (2006.01)
(Continued)

(52) U.S. Cl.
CPC ............... *C07C 17/04* (2013.01); *B01J 19/26* (2013.01); *C07C 17/013* (2013.01); *C07C 19/01* (2013.01);
(Continued)

(58) Field of Classification Search
CPC ........ C07C 17/013; C07C 17/02; C07C 17/04
See application file for complete search history.

(56) References Cited

U.S. PATENT DOCUMENTS

| 3,932,544 A | 1/1976 | Lovelace |
| 4,034,049 A * | 7/1977 | Lovelace ............... C07C 17/04 570/247 |
| 2011/0071325 A1 | 3/2011 | Ohno et al. |

FOREIGN PATENT DOCUMENTS

| GB | 1019150 A | 2/1966 |
| JP | 51-11082 B1 | 4/1976 |

(Continued)

OTHER PUBLICATIONS

International search report for PCT/JP2019/008097 dated May 21, 2019.
(Continued)

*Primary Examiner* — Medhanit W Bahta
(74) *Attorney, Agent, or Firm* — Sughrue Mion, PLLC

(57) ABSTRACT

Provided are a method and an apparatus for producing 1,2,3,4-tetrachlorobutane that are unlikely to lose 3,4-dichloro-1-butene as the material or 1,2,3,4-tetrachlorobutane as the product and can be stably and economically produce 1,2,3,4-tetrachlorobutane. A reaction liquid (1) containing 3,4-dichloro-1-butene is placed in a reaction container (11), then chlorine gas is supplied to a gas phase (2) in the reaction container (11), and the 3,4-dichloro-1-butene is reacted with the chlorine gas to give 1,2,3,4-tetrachlorobutane.

7 Claims, 1 Drawing Sheet

(51) Int. Cl.
*C07C 19/01* (2006.01)
*B01J 19/26* (2006.01)
*B01J 4/00* (2006.01)
*B01J 19/24* (2006.01)
*B01J 10/00* (2006.01)

(52) U.S. Cl.
CPC ............... *B01J 4/002* (2013.01); *B01J 10/00* (2013.01); *B01J 19/24* (2013.01); *B01J 2219/00182* (2013.01)

(56) References Cited

FOREIGN PATENT DOCUMENTS

JP     5528334 B2    6/2014
WO    2005/023734 A1    3/2005

OTHER PUBLICATIONS

International Preliminary Report on Patentability dated Sep. 22, 2020 from the International Bureau in International Application No. PCT/JP2019/008097.

* cited by examiner

METHOD AND APPARATUS FOR PRODUCING 1,2,3,4-TETRACHLOROBUTANE

CROSS-REFERENCE TO RELATED APPLICATIONS

This application is a National Stage of International Application No. PCT/JP2019/008097 filed Mar. 1, 2019, which claims priority under U.S.C. § 119(a) to Japanese Patent Application No. 2018-52451 filed Mar. 20, 2018.

TECHNICAL FIELD

The present invention relates to a method and an apparatus for producing 1,2,3,4-tetrachlorobutane.

BACKGROUND ART 1,2,3,4-Tetrachlorobutane (hereinafter also called "TCB") is produced by chlorination of 3,4-dichloro-1-butene, but the chlorination reaction, which is addition reaction of chlorine to a double bond, is an exothermic reaction and proceeds at a high rate. In order to prevent a reaction liquid from flowing back into an chlorine gas exhaust nozzle of a chlorine gas inlet tube for blowing chlorine gas into a reaction liquid, a chlorine gas diluted with an inert gas such as nitrogen gas is required to be blown into the reaction liquid to reduce the reaction rate. Consequently, the inert gas is accumulated in a reaction container, and thus the reaction is required to be performed while the inert gas is discharged from the reaction container. When the inert gas is discharged, 3,4-dichloro-1-butene and TCB are also discharged, and the material or the product may be lost, unfortunately.

Depending on reaction conditions, the resulting TCB may solidify in a reaction liquid to obstruct the chlorine gas inlet tube, and thus the above chlorination reaction may fail to stably and economically produce TCB. In other words, TCB includes optical isomers, a d-form, an l-form, and a meso-form, and the dl-forms have a melting point of 0° C. or less and are liquid at room temperature, whereas the meso-form has a melting point of about 73° C. and is solid at room temperature. Hence, the TCB has various solidification temperatures depending on ratios of the meso-form to the dl-forms. For example, when having a high meso-form ratio, the TCB partly solidifies at room temperature.

For example, PTL 1 discloses that a solidified TCB has disadvantages in industrial production of a compound, and reaction of TCB with fluorine is desirably performed with a TCB having a meso-form ratio of 60% by mass or less. A TCB having a meso-form ratio of 60% by mass or less can be prevented from solidifying, and thus the temperature when the TCB is dissolved in a reaction solvent and the reaction temperature can be set at low.

A reason why the meso-form is formed in a large amount depending on reaction conditions is supposed to be mixing of iron chloride or the like in a reaction liquid. PTL 2 discloses that the meso-form TCB is formed at a higher ratio when a catalyst of 0.1 to 20% by mass of iron chloride supported on silica gel is placed in a reaction field in the reaction of 3,4-dichloro-1-butene with chlorine. In order to reduce the meso-form ratio to prevent solidification of TCB in the reaction of 3,4-dichloro-1-butene with chlorine, therefore, it has been thought that use of a metal such as iron is required to be avoided as the material of a reaction container in which the reaction is performed.

CITATION LIST

Patent Literature

PTL 1: JP 5528334 B
PTL 2: GB 1019150 A

SUMMARY OF INVENTION

Technical Problem

As the reaction container in which the reaction of 3,4-dichloro-1-butene with chlorine is performed, a metal reaction container with a fluorocarbon resin lining or a glass reaction container is typically used. Such a reaction container is likely to be damaged, for example, swelling of a fluorocarbon resin or cracking of glass is likely to be caused, unfortunately. Hence, use of such a reaction container is not considered to be industrially advantageous.

The present invention is intended to provide a method and an apparatus for producing 1,2,3,4-tetrachlorobutane that are unlikely to lose 3,4-dichloro-1-butene as the material or 1,2,3,4-tetrachlorobutane as the product and can be stably and economically produce 1,2,3,4-tetrachlorobutane.

Solution to Problem

To solve the problems, aspects of the present invention are the following [1] to [6].

[1] A method for producing 1,2,3,4-tetrachlorobutane, the method including placing a reaction liquid containing 3,4-dichloro-1-butene in a reaction container, then supplying chlorine gas to a gas phase in the reaction container, and reacting the 3,4-dichloro-1-butene with the chlorine gas.

[2] The method for producing 1,2,3,4-tetrachlorobutane according to the aspect [1], in which the chlorine gas is supplied at an amount of 5.0 mol/h/cm$^2$ or less per unit area of a liquid surface of the reaction liquid in the reaction container.

[3] The method for producing 1,2,3,4-tetrachlorobutane according to the aspect [1] or [2], in which a pressure in the reaction container is 0.01 MPa or more and 1.0 MPa or less.

[4] The method for producing 1,2,3,4-tetrachlorobutane according to any one of the aspects [1] to [3], in which in the reaction of the 3,4-dichloro-1-butene with the chlorine gas, a portion of the reaction liquid is extracted and is returned to the gas phase in the reaction container.

[5] The method for producing 1,2,3,4-tetrachlorobutane according to the aspect [4], in which when a portion of the reaction liquid is returned to the gas phase in the reaction container, the portion of the reaction liquid is sprayed to the gas phase in the reaction container.

[6] An apparatus for producing 1,2,3,4-tetrachlorobutane by the method for producing 1,2,3,4-tetrachlorobutane according to any one of the aspects [1] to [5], the apparatus including a reaction container configured to store a reaction liquid containing 3,4-dichloro-1-butene, and a chlorine gas inlet tube configured to introduce chlorine gas into the reaction container, in the apparatus for producing 1,2,3,4-tetrachlorobutane, the chlorine gas inlet tube has a chlorine gas exhaust nozzle capable of being provided above a liquid surface of the reaction liquid in the reaction container.

Advantageous Effects of Invention

The present invention enables stable and economic production of 1,2,3,4-tetrachlorobutane while 3,4-dichloro-1- butene as the material or 1,2,3,4-tetrachlorobutane as the product is unlikely to be lost.

DESCRIPTION OF EMBODIMENTS

An embodiment of the present invention will now be described with reference to drawings. The present embodiment is merely an example of the present invention, and the present invention is not limited to the present embodiment. Various modifications or improvements can be made in the present embodiment, and such various modifications and improvements can be encompassed by the present invention.

Studies by the inventors of the present invention have revealed that a reaction of reacting 3,4-dichloro-1-butene with chlorine gas to synthesize TCB dominantly yields a solid meso-form over a liquid d-form and a liquid l-form in the resulting TCB when the reaction system contains a solid component such as iron chloride. The solid meso-form TCB unfortunately causes obstruction of a chlorine gas exhaust nozzle of a chlorine gas inlet tube for introducing chlorine gas into a reaction container or causes obstruction of a tube for conveying a reaction liquid after completion of the reaction, for example.

To address such a trouble, a fluorocarbon resin lining or a glass lining has been required on the inner face of a metal reaction container to prevent metal from coming into contact with a reaction liquid in the reaction container, and a shell and tube type heat exchanger made from Teflon (registered trademark) has also been required as the heat exchanger for cooling a reaction liquid. However, when the heat exchanger is used for a long time, unfortunately, a Teflon (registered trademark) tube of the heat exchanger may swell to have a hole due to 3,4-dichloro-1-butene, for example.

In addition, conventionally, a chlorine gas diluted with nitrogen gas is introduced into a reaction liquid, and thus 3,4-dichloro-1-butene as the material and TCB as the product flow out of a reaction container together with nitrogen gas and are lost, unfortunately.

The inventors of the present invention have conducted intensive studies to solve the above problems. As a result, the inventors have found that by introducing chlorine gas to a gas phase over the liquid surface of a reaction liquid in a reaction container, the loss of 3,4-dichloro-1-butene as the material and TCB as the product can be suppressed, and the production of the meso-form TCB can be suppressed, and have completed the present invention.

Figure 1:
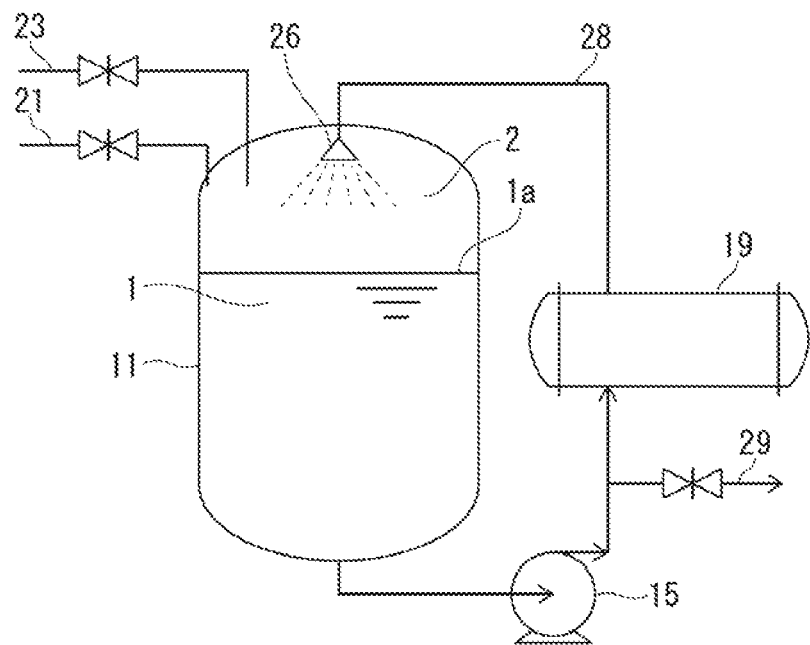
FIG. 1 is a view illustrating an embodiment of a method for producing 1,2,3,4-tetrachlorobutane pertaining to the present invention and is a schematic view illustrating a structure of an apparatus for producing 1,2,3,4-tetrachlorobutane.

In other words, a method for producing 1,2,3,4-tetrachlorobutane pertaining to the present embodiment includes placing a reaction liquid 1 containing 3,4-dichloro-1-butene in a reaction container 11, then supplying chlorine gas to a gas phase 2 in the reaction container 11, and reacting the 3,4-dichloro-1-butene with the chlorine gas to give 1,2,3,4-tetrachlorobutane (see FIG. 1).

According to the method for producing 1,2,3,4-tetrachlorobutane pertaining to the present embodiment, the reaction field can be limited to a gas-liquid interface. When a solid component such as iron chloride, which accelerates the formation of the meso-form, is present in a reaction liquid but is absent on the gas-liquid interface as the reaction field, the solid component cannot contribute to an increase of the meso-form. In the related art, a metal reaction container has been required to have a fluorocarbon resin lining or a glass lining. In the present embodiment, a metal reaction container 11 without treatment of fluorocarbon resin lining or glass lining can be used in the reaction.

As described above, the method for producing 1,2,3,4-tetrachlorobutane pertaining to the present embodiment is unlikely to yield the meso-form TCB and thus is unlikely to cause obstruction of a chlorine gas exhaust nozzle of a chlorine gas inlet tube 23 or obstruction of a tube for conveying a reaction liquid 1 after completion of the reaction, for example. Accordingly, 1,2,3,4-tetrachlorobutane can be produced stably and economically. 1,2,3,4-Tetrachlorobutane can be used as a material for synthesizing hexafluoro-1,3-butadiene through 1,2,3,4-tetrachloro-1,1,2,3,4,4-hexafluorobutane. A large amount of hexafluoro-1,3-butadiene is used as an etching gas in semiconductor production processes, and thus a method of stably and economically producing TCB is very useful.

The chlorine gas used in the reaction may have any concentration, but a chlorine gas diluted with an inert gas such as nitrogen gas is not required to be used. Hence, use of non-diluted chlorine gas can eliminate a discharge gas discharged from the gas phase 2 in the reaction container 11. Accordingly, 3,4-dichloro-1-butene as the material or 1,2,3,4-tetrachlorobutane as the product is unlikely to be lost, and an apparatus for detoxifying an outflow chlorine gas can be eliminated.

A gas discharge tube (not illustrated) for discharging the gas phase 2 in the reaction container 11 outside the reaction container 11 or a nitrogen supply tube (not illustrated) for introducing nitrogen gas into the reaction container 11 is not specifically needed in the reaction but may be provided for maintenance of the reaction container 11 or for prevention of a negative pressure when a reaction liquid 1 is discharged. As the reaction amount of chlorine gas is reduced in the reaction, the pressure in the reaction container 11 (reaction pressure) increases, but a higher reaction pressure increases the amount of chlorine gas dissolved in the reaction liquid, and this improves the reaction amount to stop the increase of the reaction pressure. Hence, such a condition causes no problem.

When chlorine gas is not diluted with an inert gas such as nitrogen gas but is used for the reaction, the supplied chlorine gas is rapidly consumed by the reaction, and thus the reaction proceeds while the pressure previously adjusted by an inert gas such as nitrogen gas is maintained. Hence, the reaction pressure can be appropriately set. However, the reaction pressure is preferably 0.01 MPa or more and 1.0 MPa (absolute pressure) or less. When the reaction is performed at 1.0 MPa (absolute pressure) or less, the apparatus for producing 1,2,3,4-tetrachlorobutane is not required to have excess pressure-resistance.

The supplied amount of chlorine gas is preferably 0.01 mol/h/cm$^2$ or more and 5.0 mol/h/cm$^2$ or less and more preferably 0.01 mol/h/cm$^2$ or more and 2.5 mol/h/cm$^2$ or less per unit area of the liquid surface 1a of a reaction liquid 1 in the reaction container 11. When the supplied amount of chlorine gas is 5.0 mol/h/cm$^2$ or less, the rising rate of the reaction pressure does not exceed the reaction rate, and an excessively high reaction pressure is prevented. Hence, the apparatus for producing 1,2,3,4-tetrachlorobutane is not required to have high pressure-resistance and is economical.

In the method for producing 1,2,3,4-tetrachlorobutane pertaining to the present embodiment, the reaction liquid 1 may be stirred or is not necessarily stirred during the reaction. In other words, the apparatus for producing 1,2,3,4-tetrachlorobutane pertaining to the present embodiment is an apparatus for producing 1,2,3,4-tetrachlorobutane by the method for producing 1,2,3,4-tetrachlorobutane pertaining to the present embodiment and includes a reaction container 11 for storing a reaction liquid 1 containing 3,4-dichloro-1-butene and a chlorine gas inlet tube 23 for introducing chlorine gas into the reaction container 11 and may or may not include a stirrer for stirring the reaction liquid 1.

When the apparatus for producing 1,2,3,4-tetrachlorobutane pertaining to the present embodiment includes a circulator that extracts a portion of the reaction liquid 1 in the reaction container 11 outside the reaction container 11 and returns the liquid into the reaction container 11 during the reaction, the stirrer for stirring the reaction liquid 1 is not necessarily included. For example, when an apparatus enables such an operation for removal of reaction heat that a portion of the reaction liquid 1 is extracted outside the reaction container 11, then is cooled by a heat exchanger 19, and is returned into the reaction container 11, the reaction liquid 1 is not necessarily stirred with a stirrer.

When a reaction liquid 1 is stirred, the stirring is preferably performed at such a low stirring rate as to prevent a solid component including iron chloride or the like contained in the reaction liquid 1 from approaching the liquid surface 1a of the reaction liquid 1. The reaction field is the liquid surface 1a of the reaction liquid 1, and thus in order to cool the vicinity of the liquid surface of the reaction liquid 1, a cooled reaction liquid 1 circulated as described above may be sprayed from a nozzle 26 when returned into the reaction container 11. In other words, the cooled reaction liquid may be blown in a spray of fine liquid drops and be spread on the liquid surface 1a of the reaction liquid 1 in the reaction container 11. Alternatively, a stirrer for stirring a reaction liquid 1 in the reaction container 11 may be included.

The metal forming the inner face of the reaction container 11 preferably has corrosion resistance against chlorine gas, hydrogen chloride, and hydrochloric acid, and examples include at least one metal selected from an iron alloy, nickel, a nickel alloy, and tantalum. These metals may be used singly or in combination of two or more of them. Examples of the iron alloy include stainless steels such as SUS316L, and examples of the nickel alloy include Hastelloy (registered trademark) and Monel (registered trademark).

The inner face of the reaction container 11 may be subjected to at least one of polishing treatment and acid washing treatment. Examples of the polishing treatment include a polishing treatment using an abrasive paper including an abrasive having a larger grain size than P150. Examples of the acid washing treatment include a treatment of washing a surface with an acid such as nitric acid and sulfuric acid. Metal surfaces other than the inner face of the reaction container 11 in the apparatus for producing 1,2,3,4-tetrachlorobutane may be subjected to at least one of polishing treatment and acid washing treatment.

If a reaction container 11 has rust or impurities on a metal surface of an inner face or other portions, the rust or impurities fall off and float in a reaction liquid 1, and the rust or impurities are supplied to a site where chlorine gas is introduced and reaction is mainly caused. When the rust or impurities are, for example, a substance containing iron, the substance is reacted with water and hydrogen chloride to form iron oxide or is reacted with chlorine gas to form iron chloride. The formed iron oxide or iron chloride then exhibits catalytic action to increase the meso-form formation ratio.

In the apparatus for producing 1,2,3,4-tetrachlorobutane of the present embodiment, a reaction liquid extraction tube 29 for extracting a reaction liquid 1 outside the reaction container 11 may be attached to the reaction container 11. In addition, typical devices required for operation of the apparatus for producing 1,2,3,4-tetrachlorobutane, including a temperature measurement device such as a thermocouple for measuring the temperature of a reaction liquid 1, a pressure gauge for measuring the pressures of sections such as the inside of the reaction container 11, and a flowmeter for measuring the flow rate of a liquid flowing through each tube, may be attached to the apparatus for producing 1,2,3,4-tetrachlorobutane.

The reaction container 11 may have any shape but preferably has a cylinder shape having a large diameter for a larger area of the liquid surface 1a of a reaction liquid 1 in the reaction container 11.

The purity of 3,4-dichloro-1-butene as the material is preferably 90% by mass or more.

The reaction of 3,4-dichloro-1-butene with chlorine gas may be performed without solvent or in a solvent. When the reaction is performed without solvent, 3,4-dichloro-1-butene is used as a reaction liquid 1, and the reaction is performed while chlorine gas is introduced to the gas phase 2 over the liquid surface 1a of the reaction liquid 1. When the reaction is performed in a solvent, a solution of 3,4-dichloro-1-butene dissolved in a solvent is used as a reaction liquid 1, and the reaction is performed while chlorine gas is introduced to the gas phase 2 over the liquid surface 1a of the reaction liquid 1. The solvent may be any type, and 1,2,3,4-tetrachloro-1,1,2,3,4,4-hexafluorobutane, carbon tetrachloride, or the like can be used.

In the resulting TCB, the meso-form formation ratio is independent of the presence or absence of a solvent, but the concentration of the meso-form in a reaction liquid 1 affects the solidification temperature of the meso-form, and thus the amount of a solvent is adjusted depending on a handling temperature of the reaction liquid 1.

EXAMPLES

The present invention will next be described more specifically with reference to examples and comparative examples.

Example 1

The structure of an apparatus for producing 1,2,3,4-tetrachlorobutane used in Example 1 will first be described with reference to FIG. 1. The apparatus for producing 1,2,3,4-tetrachlorobutane illustrated in FIG. 1 includes a reaction container 11 in which a reaction liquid 1 containing 3,4-dichloro-1-butene is stored and 3,4-dichloro-1-butene is reacted with chlorine gas, a reaction liquid introduction tube 21 for introducing a reaction liquid 1 containing 3,4-dichloro-1-butene to the reaction container 11, and a chlorine gas inlet tube 23 for introducing chlorine gas to a gas phase 2 in the reaction container 11.

A chlorine gas exhaust nozzle of the chlorine gas inlet tube 23 is provided above a liquid surface 1a of the reaction liquid 1 in the reaction container 11 and is configured to introduce chlorine gas to the gas phase 2 over the liquid surface 1a. The vertical position of the chlorine gas exhaust nozzle of the chlorine gas inlet tube 23 is variable, and the vertical position of the chlorine gas exhaust nozzle of the chlorine gas inlet tube 23 can be appropriately changed depending on the amount of a reaction liquid 1 in the reaction container 11 (i.e., the height of the liquid surface 1a of a reaction liquid 1).

To the chlorine gas inlet tube 23, a nitrogen gas tube (not illustrated) is connected in a branched manner. Through the nitrogen gas tube, nitrogen gas can be introduced to the chlorine gas inlet tube 23, then the nitrogen gas can be mixed with chlorine gas to prepare a mixed gas in which the chlorine gas is diluted with the nitrogen gas, and the mixed gas can be introduced through the chlorine gas inlet tube 23 to the gas phase 2.

The apparatus for producing 1,2,3,4-tetrachlorobutane illustrated in FIG. 1 further includes a circulator that extracts a portion of a reaction liquid 1 in the reaction container 11 during reaction outside the reaction container 11, then subjects the extracted liquid to a treatment such as filtration and cooling, and returns the treated liquid into the reaction container 11. Specifically, to the reaction container 11, both ends of a circulation tube 28 are connected such that a reaction liquid 1 can be sent by a liquid circulation pump 15 provided on the circulation tube 28, and the reaction liquid 1 extracted from the reaction container 11 can be returned through the circulation tube 28 into the container 11.

At a downstream side of the liquid circulation pump 15, a heat exchanger 19 is provided and can cool the extracted reaction liquid 1. The cooled reaction liquid 1 is returned through the circulation tube 28 into the reaction container 11. In other words, the apparatus for producing 1,2,3,4-tetrachlorobutane illustrated in FIG. 1 is configured to perform the reaction while an operation of extracting and cooling a portion of a reaction liquid 1 in the reaction container 11 and returning the cooled reaction liquid 1 to the reaction container 11 is performed.

The reaction liquid 1 returned to the reaction container 11 may be in any form. In the example in FIG. 1, the cooled reaction liquid 1 can be blown in a spray form of fine liquid drops from a nozzle 26 provided at an end of the circulation tube 28, can be sprayed to a gas phase 2 in the reaction container 11, and can be spread on the liquid surface 1a of the reaction liquid 1 in the reaction container 11.

The reaction container 11 has an inner diameter of 1 m and a height of 0.9 m, and the liquid surface 1a of a reaction liquid 1 placed in the reaction container 11 has an area of 0.78 m$^2$. The vertical position of the chlorine gas exhaust nozzle of the chlorine gas inlet tube 23 is 15 cm above the liquid surface 1a of a reaction liquid 1. The whole reaction container 11 including the inner face is formed from stainless steel SUS316. Before use of the apparatus for producing 1,2,3,4-tetrachlorobutane for reaction, the inner face of the reaction container 11 was polished with an abrasive paper including an abrasive having a larger grain size than P240, then was washed with an acid, and was dried by a nitrogen gas stream.

The apparatus for producing 1,2,3,4-tetrachlorobutane described above was used to perform reaction, giving 1,2,3,4-tetrachlorobutane. In the reaction container 11, 550 kg (4,400.4 mol) of 3,4-dichloro-1-butene was placed as a reaction liquid 1, next the liquid temperature was adjusted at 70° C., then chlorine gas at a concentration of 100% by mole was supplied at a flow rate of 54 kg/h (761.6 mol/h) through the chlorine gas inlet tube 23 to the gas phase 2, and chlorination reaction was performed. The supplied amount of chlorine gas was 0.10 mol/h/cm$^2$ per unit area of the liquid surface 1a of the reaction liquid 1 in the reaction container 11. At the start of the chlorine gas supply, the pressure in the reaction container 11 was atmospheric pressure.

During the reaction, the reaction liquid 1 was circulated through the circulation tube 28. During the circulation, the reaction liquid 1 was sent to the heat exchanger 19 to cool the reaction liquid 1, and the temperature of the reaction liquid 1 was maintained at 70° C. during the reaction. At this point, the pressure in the reaction container 11 was substantially atmospheric pressure.

After about 5.8 hours, the pressure in the reaction container 11 was started to rise, and thus the supply of chlorine gas was stopped. At this point, the pressure in the reaction container 11 was 0.12 MPa.

After the stop of the chlorine gas supply, the pressure in the reaction container 11 decreased, and the reaction liquid 1 was analyzed, resulting in a 3,4-dichloro-1-butene conversion ratio of 100% and a TCB yield of 97% by mole in terms of 3,4-dichloro-1-butene. By-products were at 3% by mole. The resulting TCB had a meso-form ratio of 50%. The TCB yield and the meso-form ratio in TCB were determined by quantitative analysis of the reaction liquid 1 using gas chromatography (internal standard method).

Comparative Example 1

The structure of an apparatus for producing 1,2,3,4-tetrachlorobutane used in Comparative Example 1 will first be described with reference to FIG. 2. The conventional apparatus for producing 1,2,3,4-tetrachlorobutane illustrated in FIG. 2 includes a reaction container 111 in which 3,4-dichloro-1-butene is reacted with chlorine gas, a reaction liquid introduction tube 121 for introducing a reaction liquid 101 containing 3,4-dichloro-1-butene to the reaction container 111, a stirrer 113 for stirring the reaction liquid 101 in the reaction container 111, a chlorine gas tube 123 for introducing chlorine gas to the reaction liquid 101 in the reaction container 111, and a gas discharge tube 125 for discharging a gas phase 102 in the reaction container 111 outside.

As apparent from FIG. 2, a chlorine gas exhaust nozzle of the chlorine gas tube 123 is provided in the reaction liquid 101 in the reaction container 111 (below a liquid surface 101a of the reaction liquid 101), and accordingly chlorine gas is to be blown into the reaction liquid 101. A chlorine gas tube may have a plurality of chlorine gas exhaust nozzles, but the chlorine gas tube 123 in the example has a single chlorine gas exhaust nozzle.

To the chlorine gas tube 123, a nitrogen gas tube 127 is connected in a branched manner. Through the nitrogen gas tube 127, nitrogen gas can be introduced to the chlorine gas tube 123, then the nitrogen gas can be mixed with chlorine gas to prepare a mixed gas in which the chlorine gas is diluted with the nitrogen gas, and the mixed gas can be introduced through the chlorine gas tube 123 into the reaction liquid 101.

Figure 2:
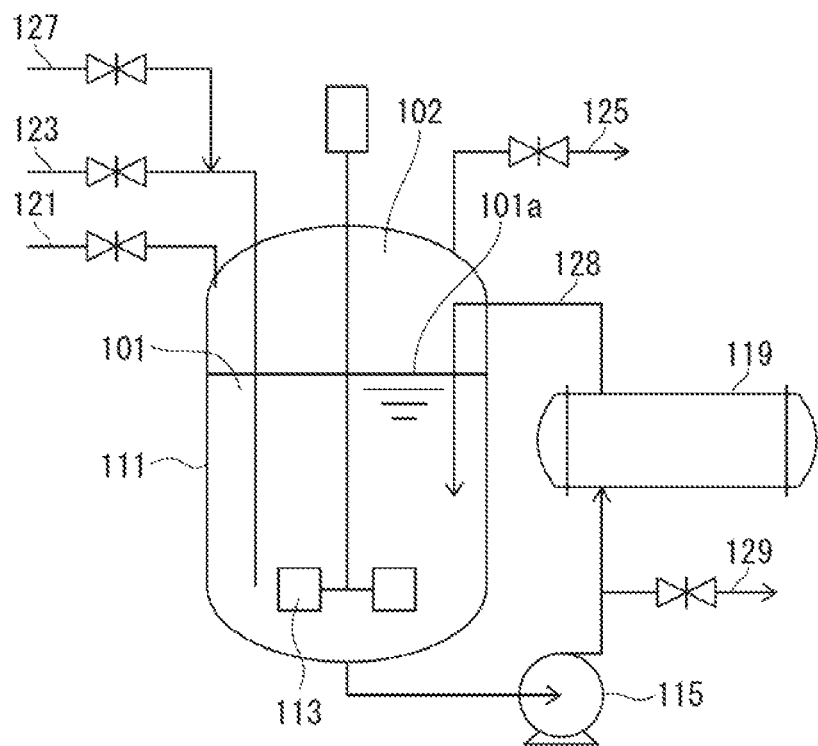
FIG. 2 is a schematic view illustrating a structure of a conventional apparatus for producing 1,2,3,4-tetrachlorobutane.

The apparatus for producing 1,2,3,4-tetrachlorobutane illustrated in FIG. 2 further includes a circulator that extracts a portion of the reaction liquid 101 in the reaction container 111 during reaction outside the reaction container 111 and returns the liquid into the reaction container 111. Specifically, to the reaction container 111, both ends of a circulation tube 128 are connected such that a reaction liquid 101 can be sent by a liquid circulation pump 115 provided on the circulation tube 128, and the reaction liquid 101 extracted from the reaction container 111 can be returned through the circulation tube 128 into the container 111. On the circulation tube 128, for example, at a downstream side of the liquid circulation pump 115, a heat exchanger 119 is provided.

To the circulation tube 128, a reaction liquid extraction tube 129 is further connected in a branched manner and is configured to extract the reaction liquid 101 outside the apparatus for producing 1,2,3,4-tetrachlorobutane but not to return the reaction liquid 101 into the reaction container 111.

The reaction container 111 has an inner diameter of 1 m and a height of 0.9 m, and the liquid surface 101a of a reaction liquid 101 placed in the reaction container 111 has an area of 0.78 m$^2$. The whole reaction container 111 including the inner face is formed from stainless steel SUS316.

The conventional apparatus for producing 1,2,3,4-tetrachlorobutane described above was used to perform reaction, giving 1,2,3,4-tetrachlorobutane. In the reaction container 111, 550 kg (4,400.4 mol) of 3,4-dichloro-1-butene was placed as a reaction liquid 101, next the liquid temperature was adjusted at 70° C., then chlorine gas at a concentration of 100% by mole was supplied at a flow rate of 20 kg/h (282.1 mol/h) into the reaction liquid 101, and chlorination reaction was performed. The chlorine gas was not diluted with nitrogen gas, and thus the reaction was performed while the valve of the gas discharge tube 125 was closed. At the start of the chlorine gas supply, the pressure in the reaction container 111 was atmospheric pressure.

During the reaction, the reaction liquid 101 was circulated through the circulation tube 128. During the circulation, the reaction liquid 101 was sent to the heat exchanger 119 to cool the reaction liquid 101, and the temperature of the reaction liquid 101 was maintained at 70° C. during the reaction. At this point, the pressure in the reaction container 11 was substantially atmospheric pressure. During the reaction, a stirrer 113 having six flat turbine blades was used to stir the reaction liquid 101. The power of the stirrer 113 was 0.044 kW relative to a volume of 1 m$^3$ of the reaction liquid 101.

After the reaction for 15.7 hours, the pressure in the reaction container 111 was started to rise, and thus the supply of chlorine gas was stopped. At this point, the pressure in the reaction container 11 was 0.12 MPa. To extract the reaction liquid 101 from the reaction container 111, nitrogen gas would have been sent from the nitrogen gas tube 127 through the chlorine gas tube 123 into the reaction container 111 to purge the inside of the reaction container 111 with nitrogen gas, but the nitrogen gas could not be sent into the reaction container 111.

This is supposed to be because the chlorine gas supply was stopped at a high pressure in the reaction container 111, thus the reaction liquid 101 flowed back into the chlorine gas tube 123, and a solid TCB precipitated in the chlorine gas tube 123 to obstruct the chlorine gas tube 123. The inside of the reaction container 111 could not be purged with nitrogen gas, and harmful substances such as chlorine gas dissolved in the reaction liquid 101 could not be removed. Accordingly, it was difficult to safely extract the reaction liquid 101.

The reaction liquid 101 was analyzed, resulting in a 3,4-dichloro-1-butene conversion ratio of 100% and a TCB yield of 97% by mole in terms of 3,4-dichloro-1-butene. The resulting TCB had a meso-form ratio of 70%. This is supposed to be because an iron component derived from the stainless steel reaction container 111 functioned as a catalyst.

Comparative Example 2

Reaction was performed in the same manner as in Comparative Example 1 except that chlorine gas was diluted with nitrogen gas to give 90% by mole chlorine gas, then the diluted chlorine gas was supplied to a reaction liquid 101, and nitrogen gas accompanied with chlorine gas was discharged outside the reaction container 111 through the gas discharge tube 125. The flow rate of chlorine gas was 20 kg/h as with Comparative Example 1.

After the reaction for 16 hours, the nitrogen gas supply was not stopped, but the chlorine gas supply was stopped. Accordingly, the chlorine gas tube 123 was not obstructed, and the inside of the reaction container 111 was able to be purged with nitrogen gas. The reaction liquid 101 was analyzed, and unreacted 3,4-dichloro-1-butene was not detected. Hence, the 3,4-dichloro-1-butene conversion ratio was 100% as an output record, but the TCB yield was 79% by mole in terms of 3,4-dichloro-1-butene. The decrease in yield was caused also by discharge of some of the supplied 3,4-dichloro-1-butene together with nitrogen gas through the gas discharge tube 125. The resulting TCB had a meso-form ratio of 70%.

REFERENCE SIGNS LIST 1 reaction liquid
1a liquid surface
2 gas phase
11 reaction container
23 chlorine gas inlet tube

The invention claimed is:

1. A method for producing 1,2,3,4-tetrachlorobutane, the method comprising:
placing a reaction liquid containing 3,4-dichloro-1-butene in a reaction container; then
supplying chlorine gas to a gas phase in the reaction container; and
reacting the 3,4-dichloro-1-butene with the chlorine gas;
wherein the chlorine gas is supplied at an amount of 5.0 mol/h/cm$^2$ or less per unit area of a liquid surface of the reaction liquid in the reaction container.

2. The method for producing 1,2,3,4-tetrachlorobutane according to claim 1, wherein a pressure in the reaction container is 0.01 MPa or more and 1.0 MPa or less.

3. The method for producing 1,2,3,4-tetrachlorobutane according to claim 1, wherein in the reaction of the 3,4-dichloro-1-butene with the chlorine gas, a portion of the reaction liquid is extracted and is returned to the gas phase in the reaction container.

4. The method for producing 1,2,3,4-tetrachlorobutane according to claim 3, wherein when a portion of the reaction liquid is returned to the gas phase in the reaction container, the portion of the reaction liquid is sprayed to the gas phase in the reaction container.

5. The method for producing 1,2,3,4-tetrachlorobutane according to claim 1, wherein a pressure in the reaction container is 1.0 MPa or less.

6. The method for producing 1,2,3,4-tetrachlorobutane according to claim 5, wherein in the reaction of the 3,4-dichloro-1-butene with the chlorine gas, a portion of the reaction liquid is extracted and is returned to the gas phase in the reaction container.

7. The method for producing 1,2,3,4-tetrachlorobutane according to claim 2, wherein in the reaction of the 3,4-dichloro-1-butene with the chlorine gas, a portion of the reaction liquid is extracted and is returned to the gas phase in the reaction container.

* * * * *